United States Patent [19]

Hagiwara et al.

[11] Patent Number: 5,338,838
[45] Date of Patent: Aug. 16, 1994

[54] ANTIOXIDATION ACTIVE SUBSTANCE AND UTILIZATION THEREOF

[75] Inventors: Yoshihide Hagiwara; Hideaki Hagiwara, both of Takarazuka, Japan

[73] Assignee: Yoshihide Hagiwara, Takarazuka, Japan

[21] Appl. No.: 893,069

[22] Filed: Jun. 3, 1992

Related U.S. Application Data

[62] Division of Ser. No. 745,251, Aug. 14, 1991.

[30] Foreign Application Priority Data

| | | | |
|---|---|---|---|
| Aug. 17, 1990 | [JP] | Japan | 2-217344 |
| Aug. 21, 1990 | [JP] | Japan | 2-220398 |
| Mar. 1, 1991 | [JP] | Japan | 3-059374 |
| Mar. 4, 1991 | [JP] | Japan | 3-062558 |
| Mar. 4, 1991 | [JP] | Japan | 3-062688 |

[51] Int. Cl.$^5$ .................. C07H 17/08; C07H 1/08
[52] U.S. Cl. ........................ 536/8; 536/4.1; 424/195.1
[58] Field of Search ............... 536/4.1, 8, 124; 424/195.1

[56] References Cited

U.S. PATENT DOCUMENTS

| | | | |
|---|---|---|---|
| 3,878,191 | 4/1975 | Fukumoto et al. | 536/8 |
| 4,942,033 | 7/1990 | Aubert et al. | 424/195.1 |

FOREIGN PATENT DOCUMENTS

| | | | |
|---|---|---|---|
| 0271133 | 6/1988 | European Pat. Off. | C09K 15/34 |
| 62-026293 | of 0000 | Japan . | |
| 179678 | of 0000 | Japan . | |

OTHER PUBLICATIONS

Hilsenbeck et al; Phytochemistry 22(10):2215–2217 (1983).
Ramarathnam et al; J. Agric. Food Chem. 37: 316–319 (1989).
Besson et al; Chemical Abstracts 91:207481g (1979).
McCormick et al; Chemical Abstracts 95:200563; (1981).
Chaboud et al; Chemical Abstracts 106:815902 (1987).
Ramarathnam et al; Chemical Abstracts 110:133921n (1989).
Li et al; J. Chromatog, 562:435–446 (1991).
Hilsenbeck et al; Phytochemistry 29(7):2181–5 (Jun. 4, 1990).
Tschesche et al. Chemische Berichte, 109:2901–2907, 1976.
Ramaratonamu et al. Chem. Abs. 112:34694a, 1990.

*Primary Examiner*—Johnnie R. Brown
*Assistant Examiner*—Howard C. Lee
*Attorney, Agent, or Firm*—Sherman and Shalloway

[57] ABSTRACT

An antioxidant substance which is a green leaf component in a green plant, comprising a component which is substantially insoluble in n-hexane but soluble in an aqueous ethanol solution having a water content of 0 to 80% by volume. The substance has an antioxidant activity as potent as or more potent than α-tocopherol, and is useful as an antioxidant for use in the field of foods, and medicines. Particularly, the antioxidant substance can be used for maintaining the freshness and quality of foods or storage thereof. The substance can be blended with cosmetics for skin and hair and are useful for the prevention of spots, freckles, chapping and sunburning.

15 Claims, 11 Drawing Sheets

FIG. I

ANTIOXIDATION ACTIVE SUBSTANCE AND UTILIZATION THEREOF

This is a division of application Ser. No. 07/745,251 filed Aug. 14, 1991.

The present invention relates to an antioxidant component having a potent antioxidant activity derived from green plants, preferably green leaves of cereal, especially young green leaves of barley and to utilization of the same as an additive to foods, cosmetics and the like.

Hitherto, there have been known various antioxidants derived from natural sources or chemically synthesized and used in the field of foods medicines, cosmetics and the like which include natural antioxidants such as example, α-tocopherol, and ascorbic acid, and phenol type synthetic antioxidants such as butylhydroxyanisole (BHA), and dibutylhydroxytoluene (BHT).

On the other hand, noticing that green leaves of green plants, particularly cereals, contain components having many physiological activities such as antitumor activity, antihyperlipemic activity, hypoglycemic activity, antiviral activity and the like, the present inventors have examined various components contained for their antioxidant activity.

As a result, it has now been found that green leaf components in green leaves of green plants, for example, cereals such as barley and wheat, contain a component which has an antioxidant activity as potent as or more potent than α-tocopherol. The present invention has been achieved based on this discovery.

According to one aspect of the present invention, there is provided an antioxidant substance derived from a green leaf component in a green plant, comprising a component which is substantially insoluble in n-hexane but soluble in an aqueous ethanol solution containing 0 to 80% by volume of water.

According to another aspect of the present invention, there is provided an antioxidant substance derived from a green leaf component in a green plant, comprising a component which is substantially insoluble in n-hexane but soluble in an aqueous ethanol solution containing 0 to 80% by volume of water and in an aqueous methanol solution containing 0 to 80% by volume of water.

Hereafter, the antioxidant substances of the present invention will be described in more detail. Herein, the water content % of aqueous alcohol solution is expressed in terms of v/v %.

The green plants which can be used as raw materials may preferably be plants of Gramineae family, especially cereals such as barley and wheat. In addition, there can also be used meadow grasses such as clovers, and alfalfa, vegetables such as kale, spinach, lettuce, parsley, celery, cabbage, Chinese cabbage, mizuna (a kind of Japanese cabbage: Brassica rapa L. var. laciniifolia Kitam.), green pepper, green leaves of carrot, and green leaves of radish, non-cultivated vegetables which grow in fields or wastelands or mountains such as bamboo grass, and ashitaba (a kind of Japanese parsley: *Angelica keiskei* (Mig.) Koidz.); and further fresh-water or sea-water algae such as Spirulina, Chlorella, wakame (a Japanese sea weed: *Undaria pinnatifida Suringar*), and green laver (Enteromorpha).

As the cereals which can be used favorably in the present invention, the most preferred one is barley. Besides, wheat, rye, oats, gromwell-reed, corn, millet, Italian dye-grass can also be used.

In the present invention, fresh stems and/or leaves of young plants harvested before ripening of these green plants, especially cereals (herein these stems and/or leaves are called generally as "green leaves") are particularly suitable.

Green leaves of green plants, for example, cereals, are first sucked by a mechanical crushing means such as a mixer, a juicer or the like and then crude solid contents are removed by sifting, filtration or the like, if desired, to prepare a sucked juice (hereinafter, referred to as "green juice").

Next, the green juice as is or green juice powder obtained by drying by a suitable drying means such as lyophilization, spray-drying or the like is extracted with a sufficient amount of water or n-hexane. This extraction treatment can be performed usually at room temperature and may be repeated twice or more, if desired, thereby separating and recovering a component which is soluble in water or substantially insoluble in n-hexane. The extract component recovered may be dried and solidified in this stage in the same manner as described above.

The water-soluble component or n-hexane-insoluble component thus obtained is extracted with an aqueous ethanol solution having a water content of 0 to 80%, preferably 10 to 70%, and more preferably 15 to 50%, for example, an aqueous ethanol solution having a water content of 20% to separate and recover a component soluble in that aqueous ethanol solution.

The extraction with such aqueous ethanol solution may be performed directly on the green juice prepared as described above or water-soluble components of green leaves obtained by completely removing water-insoluble components from the green juice or powder prepared by drying such water-soluble components by a suitable drying means such as lyophilization or spray-drying.

The aqueous ethanol-soluble component may be used as an antioxidant substance of the present invention as it is or after concentration or distilling off of the solvent.

According to the present invention, the aforementioned aqueous ethanol-soluble component can be treated with a suitable adsorbent such as Styrene-DVB resin absorbent (for example, Amberlite Adsorbent XAD-2, registered trademark for a product by Rohm & Haas Co.) and eluted with an aqueous methanol solution having a water content of 0 to 80%, preferably 20 to 70%, and more preferably 30 to 60% to recover a component soluble in that aqueous methanol solution. This makes it possible to obtain a fraction having a higher antioxidant activity.

The aqueous methanol-soluble component recovered from barley as described above can be purified by recrystallization from, for example, an aqueous methanol solution having a water content of 30 to 70%, preferably 40 to 60% to obtain an active ingredient of an antioxidant substance as pale yellow crystal. The active ingredient of the antioxidant thus isolated has been identified by NMR, mass spectrometry or the like 2'-O-glucosyl-isovitexin having a structure represented by the following formula:

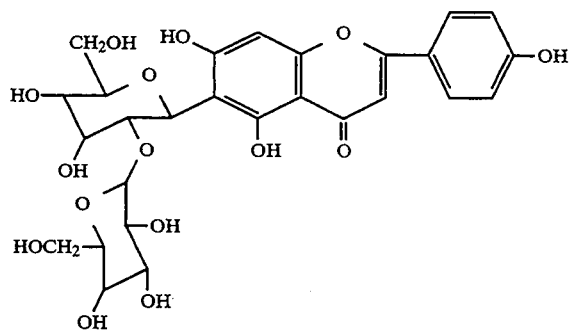

(cf. Example 1 below)

It is presumed that an antioxidant substance having the aforementioned structure or one similar thereto is contained in green leaves of various green plants such as cereals and that substance constitutes the active ingredient of the antioxidant substance of the present invention.

As will be apparent from examples hereinbelow, the antioxidant substance of the present invention has a high antioxidant activity as potent as or more potent than α-tocopherol, and is useful as an antioxidant in the field of foods, medicines and the like.

For example, the antioxidant substance of the present invention is free of various metal elements and substances promoting denaturation of foods which are usually contained in green leaves used as raw material, and hence it can be blended advantageously in various inorganic or organic materials or compositions in the field of foods, medicines and the like which requires antioxidizing properties. For example, the antioxidant substance of the present invention may be mixed with sugars such as fructose, glucose, dextrin, and starch; amino acids; organic acids such as citric acid, malic acid, tartaric acid, and succinic acid; various vitamins; colorants, perfumes, various viscosity increasing agents, and the like, after being included by cyclodextrin, crown ether or the like, if desired. In particular, the antioxidant substance of the present invention can be sterilized by filtration when it is in the form of aqueous compositions since it gives substantially no adverse influence on the solubility in water or transparency of the resulting composition.

The antioxidant substance of the present invention has advantages that it can be mixed or blended as powder prepared by spray-drying or vacuum drying or the like with a raw material for medicines, paints, cosmetics, foaming agents and the like, such as talc, zinc oxide, sodium carbonate, sodium hydrogen carbonate, titanium dioxide, kaolin, and calcium phosphate to produce novel industrial products and that it causes no change in the quality of the products. In addition, the antioxidant substance of the present invention, which is soluble in water and also in alcohols, is useful for the stabilization of inorganic and organic compositions, and makes it possible to produce excellent novel products, for example, antioxidants for the preparation of polymers; emulsion paints; cosmetics; paper products; foods; medicines; materials for medical therapy and the like.

For example, the antioxidant substance provided according to the present invention may be used for maintaining freshness and quality of or preserving various foods by blending it with the foods. Here, the term "foods" is used in a broader sense and includes not only typical foods but also beverages (including beverages), seasonings and the like, for example, fruits and their processed foods (e.g., canned fruits, bottled fruits, jams, marmalades, etc.), fishes, meats and their processed foods (e.g., hams, sausages, corned beef, etc.) breads and noodles (Japanese noodles, buckwheat noodle, Chinese noodle, spaghetti, macaronis, etc.) fruit juice, various drinkings, cookies, candies, dairy products (e.g., butter, cheese, etc.) vegetable plant fat and oils, margarine, plant proteins, retort foods, frozen foods, various seasonings (e.g., miso (bean paste), soy sauce, sauce, etc.), alcoholic beverages (e.g., fruit liquors, sake, etc.) and the like.

The antioxidant substance of the present invention is pale yellow or colorless, soluble in water and alcohols and can be well absorbed by living organisms so that it can be blended readily with the aforementioned foods without giving any substantial adverse influence on their compositions and components or appearance. For example, it can be freely blended with various additives which are often used in foods, including sweeteners such as fructose, glucose, and millet jelly; organic acid such as citric acid, malic acid, tartaric acid, and succinic acid and salts thereof; various vitamins, colorants, perfumes, various vegetable viscosity increasing agents, and the like, without giving no influence to their solubility in water and transparency, but permitting treatments such as filtration, sterilization and the like.

The antioxidant substance of the present invention can be used advantageously as an agent for retaining the freshness or quality of such foods and uptake of the antioxidant substance of the invention is helpful for the maintenance or promotion of health.

When the antioxidant substance of the present invention is used as an agent for preserving the freshness or quality of foods, the amount of the antioxidant substance may be varied within a wide range and it is difficult to set it to a specific value. However, as a guideline, it can be used in an amount of 0.1 to 10% by weight, and preferably 0.5 to 7% by weight, in the form of an extract with aqueous ethanol solution having a water content of 20%; 0.001 to 5% by weight, and preferably 0.01 to 2% weight, in the form of methanol fraction having a water content of 40%; and 0.001 to 1% by weigh, and preferably 0.005 to 0.5% by weight, in the form of 2"-O-glucosyl-isovitexin.

The antioxidant substance provided according to the present invention exhibits excellent effects on the prevention of spots (chloasma), freckles, chapping, burning with UV rays (sunburn), etc. and is safe. Hence it can be utilized for the prevention of spots (chloasma, freckles, chapping, burning with UV rays (sunburn) and protection of hair and the like by blending it with cosmetics for skins and hair.

As described above, the antioxidant substance of the present invention is pale yellow, soluble in water and alcohols and highly absorbable to living organisms, and can be readily blended with cosmetics for skin and hair, e.g., water, alcohols, aqueous alcohol solutions, lotions, creams, cream emulsions, hair tonics, hair growing agents, bath compositions, soaps, ointments and the like without giving any substantially adverse effects on their composition or appearance.

The amount of the aforementioned antioxidant substance to be blended may be varied within a wide range depending on the kind and utility of the cosmetics but generally it is suitable to blend the antioxidant substance in an amount of 0.01 to 10% by weight, and preferably 0.1 to 5% by weight, and 0.001 to 1% by weight and preferably 0.005 to 0.5% by weight as 2'-O-glucosyl-isovitexin, active ingredient, based on the weight of the matrix of the cosmetics.

The matrix which can be used in the aforementioned cosmetics is not limited particularly and there can be various matrices conventionally used in skin and hair cosmetics such as water, alcohols, propylene glycol, stearic acid, glycerol, cetyl alcohol, liquid paraffin and the like. As usual, the cosmetics may, if desired, contain one or more of vitamins, extracts from galenics, hormones and medicines for external applications, and the like.

Hereafter, the present invention will be explained more concretely by way of examples and with reference to the attached drawings.

Brief description of the drawings referred to in the examples below are as follows.

EXAMPLE 1

Fractionation and Preparation of Active Ingredient

Figure 1:
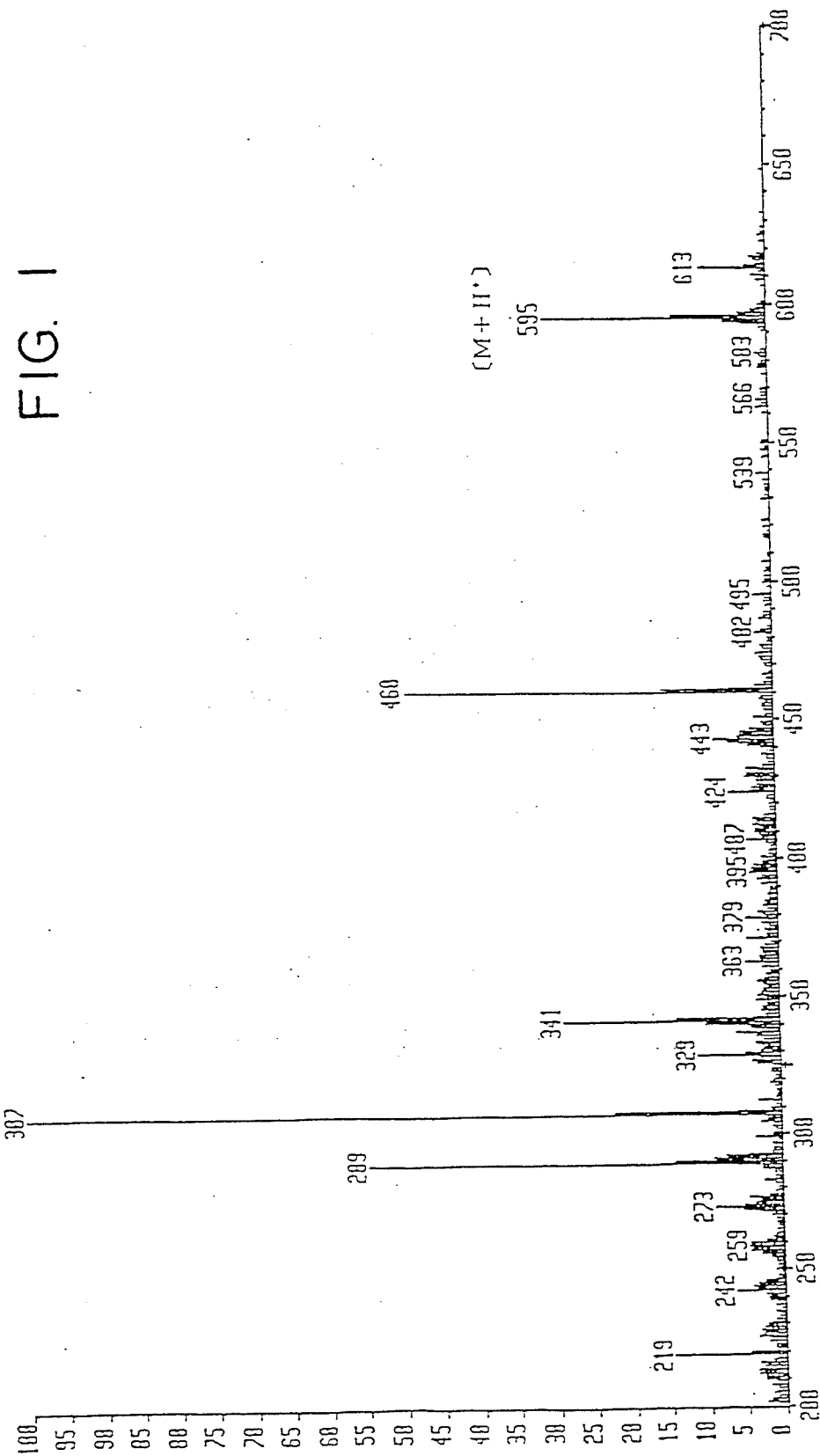
FIG. 1 is a chart illustrating results of the measurement by FAB-MS method of 2'-O-glucosyl-isovitexin obtained in Example 1.

To lyophilized powder (2.0 g) of green juice of barley before ripening was added 500 ml of n-hexane, and the mixture was stirred well at room temperature for about 5 minutes. Thereafter, insoluble matter was separated by centrifugation (8,000 rpm, 10 minutes), and 500 ml of n-hexane was added to the insoluble matter thus separated. Repeating this procedure, n-hexane-insoluble component was obtained.

The n-hexane-insoluble component was added to 500 ml of an aqueous ethanol solution having a water content of 20 v/v %. After stirring the mixture well at room temperature for about 5 minutes, insoluble matter was filtered. The insoluble matter filtered was treated again with an aqueous ethanol having a water content of 20 v/v %, and the filtrate obtained was combined with the previous filtrate, followed by evaporation of the solvent under reduced pressure. This gave 13.0 g of ethanol extract.

The ethanol-soluble content was adsorbed on Amberlite XAD-2 column, and eluted serially with deionized water, aqueous methanol solutions having water contents of 80 v/v %, 60 v/v %, 40 v/v %, 20 v/v %, and 0 v/v %, respectively, and acetone to obtain various eluates.

The respective eluates were distilled under reduced pressure to evaporate the solvents and as a result 4.77 g of water-extract, 180 mg of 20% methanol-extract, 131 mg of 40% methanol-extract, 199 mg of 60% methanol-extract, 32 mg of 80% methanol-extract, 165 mg of 100% methanol-extract, 0.87 mg of acetone-extract were obtained (here, % of methanol indicates the concentration of methanol (v/v %) in each aqueous methanol solution).

The 60% methanol-extract thus obtained was recrystallized from 60% methanol to obtain 180 mg of pale yellow crystals. The structure of the crystal was performed by mass spectrometry and NMR.

Mass spectrometry was performed by using an FAB-MS: VG ZAB-2F (Xenon Gun) (Jon Tech) type mass spectrometer, and results as shown in FIG. 1 were obtained. The mass spectrum thus obtained showed a peak of [M + H$^+$] at m/z = 595, and the molecular weight was determined to be 594. Taking this together with the results of elemental analysis, the molecular formula of the present substance was judged to be $C_{27}H_{30}O_{15}$.

Figure 2:
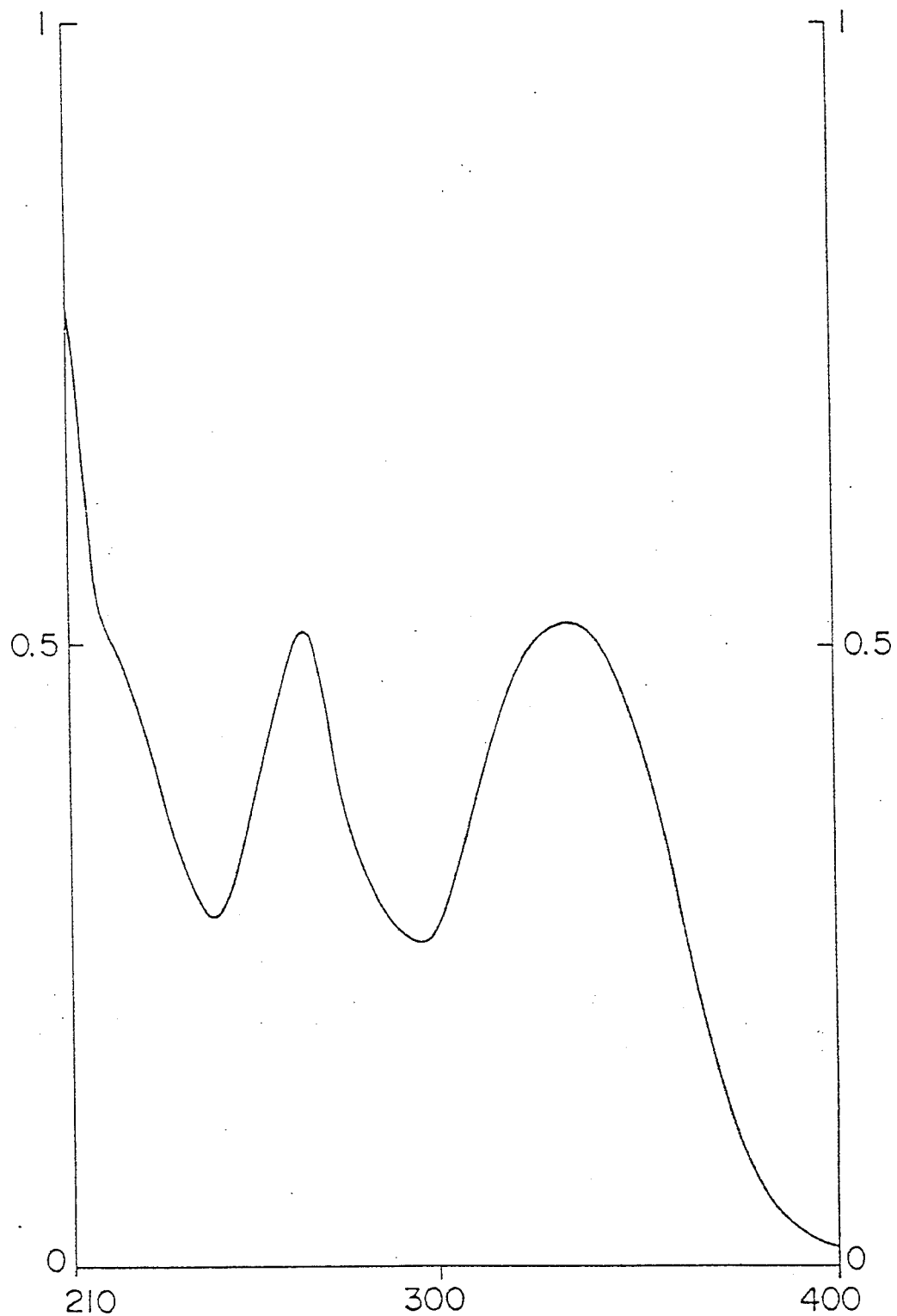
FIG. 2 is a chart illustrating a UV ray absorption spectrum of 2'-O-glucosyl-isovitexin in H2O system.
Figure 3:
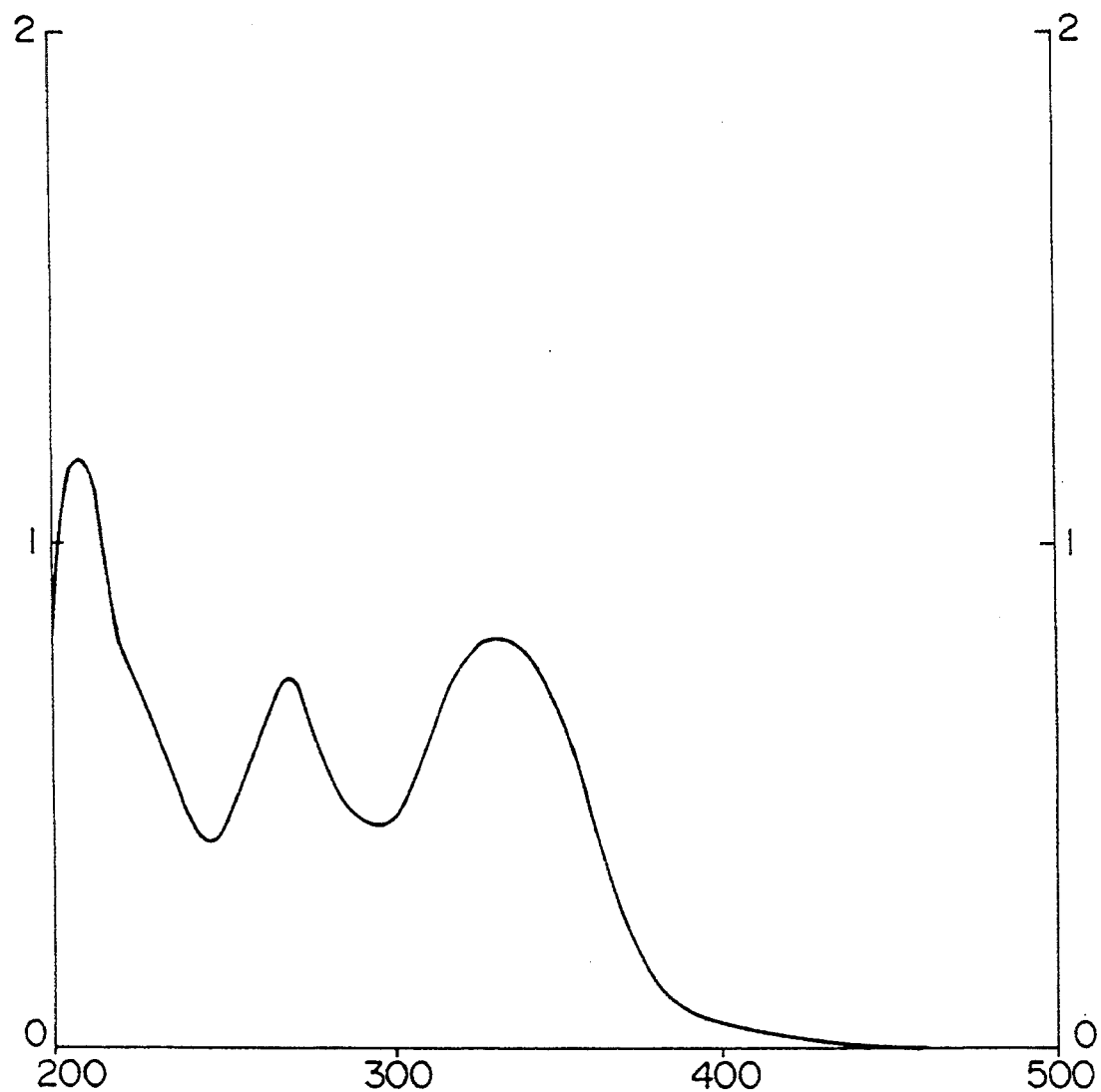
FIG. 3 is a chart illustrating a UV ray absorption spectrum of 2'-O-glucosyl-isovitexin in MeOH system.

Upon UV absorption spectrum of the present substance was measured in H$_2$O and in methanol, absorptions by flavonoid glucoside were observed as shown in FIGS. 2 and 3, respectively.

Figure 4:
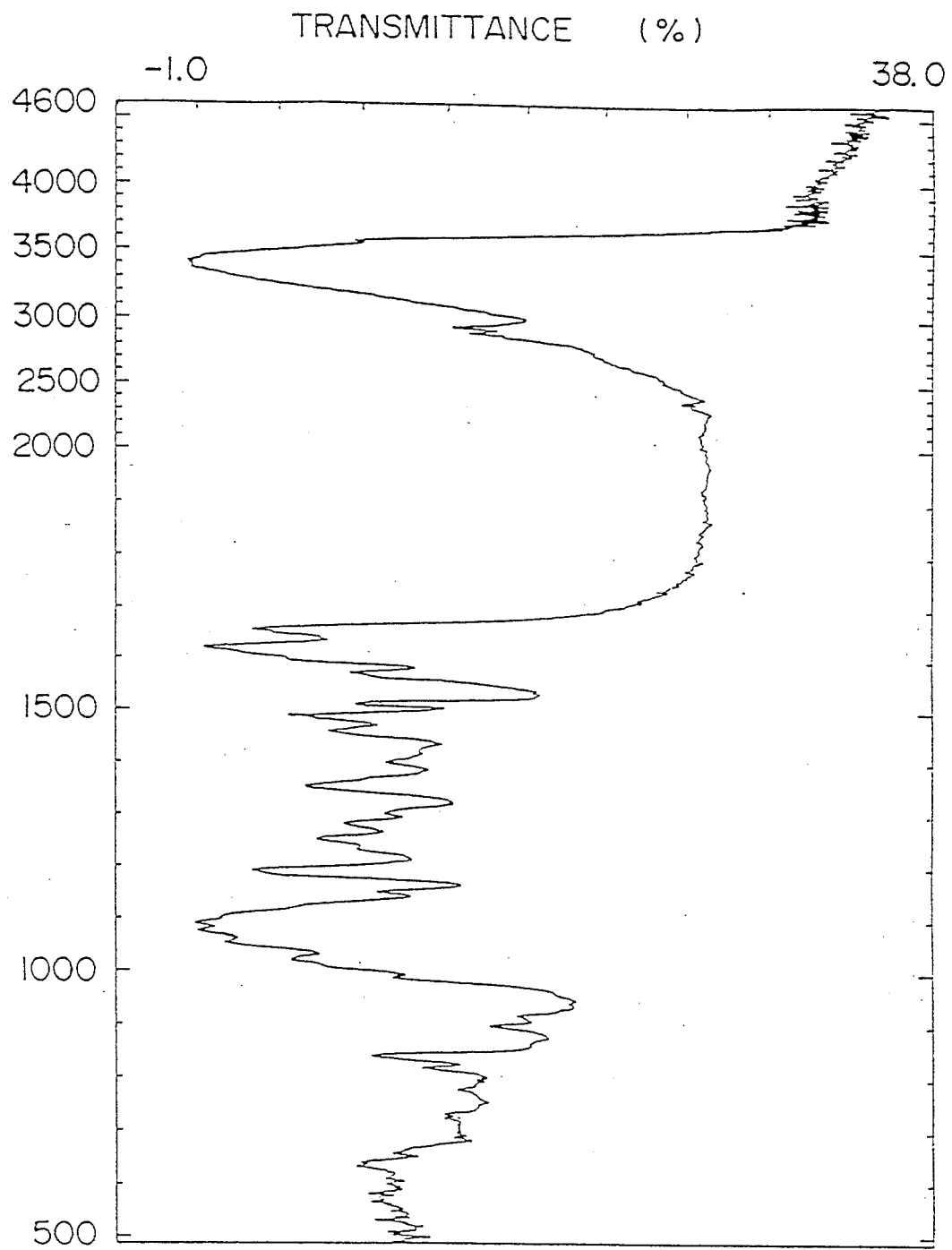
FIG. 4 is a chart illustrating an infrared absorption spectrum of 2'-O-glucosyl-isovitexin.

Infrared absorption spectrum was measured by KBr method using JASCO FT/IR-7000S and the results obtained are shown in FIG. 4. Absorption at 3422 cm$^-$ indicates the presence of OH group.

Upon hydrolysis with hydrochloric acid-methanol by a conventional method, the present substance released one molecule of glucose to produce isovitexin.

Figure 5:
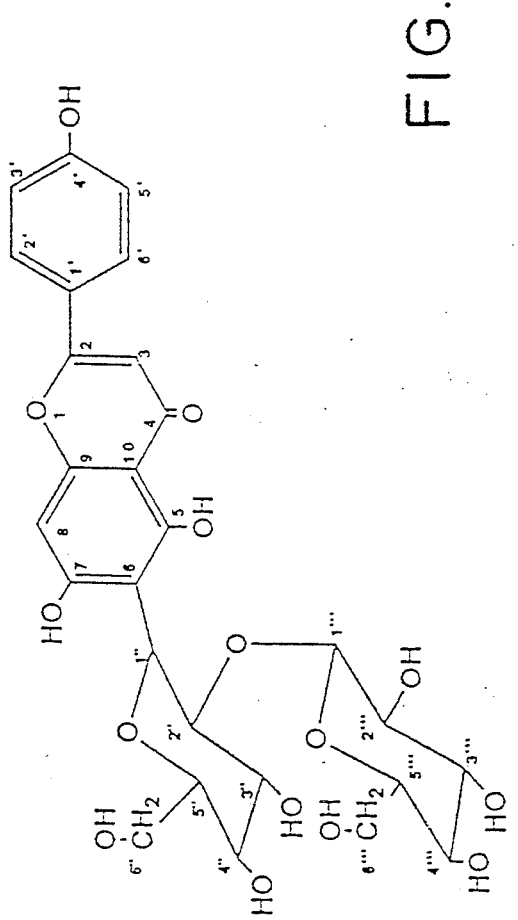
FIG. 5 is a chart illustrating results of $^{13}$C-NMR analysis of 2'-O-glucosyl-isovitexin.
Figure 5:
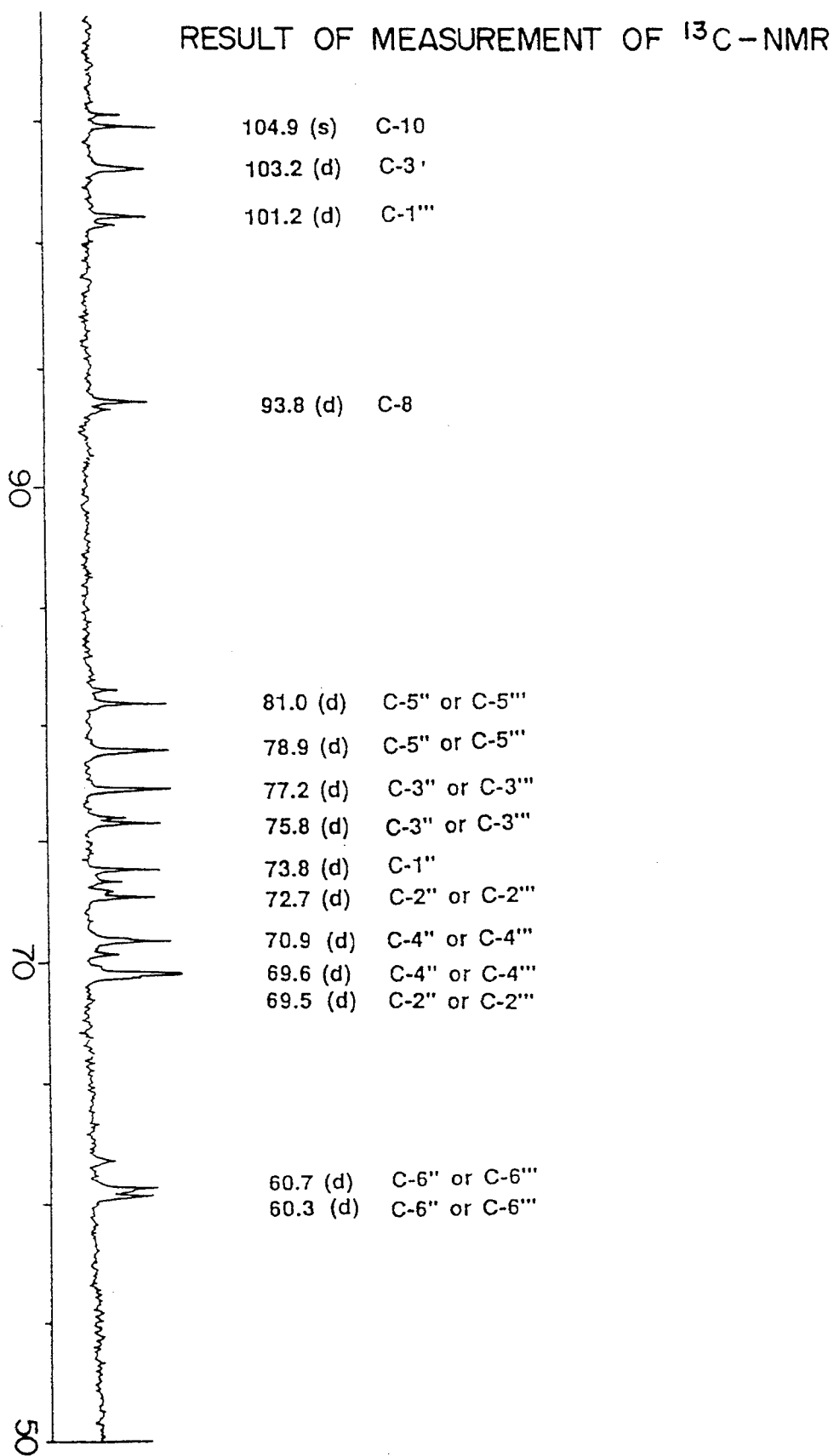
Figure 5:
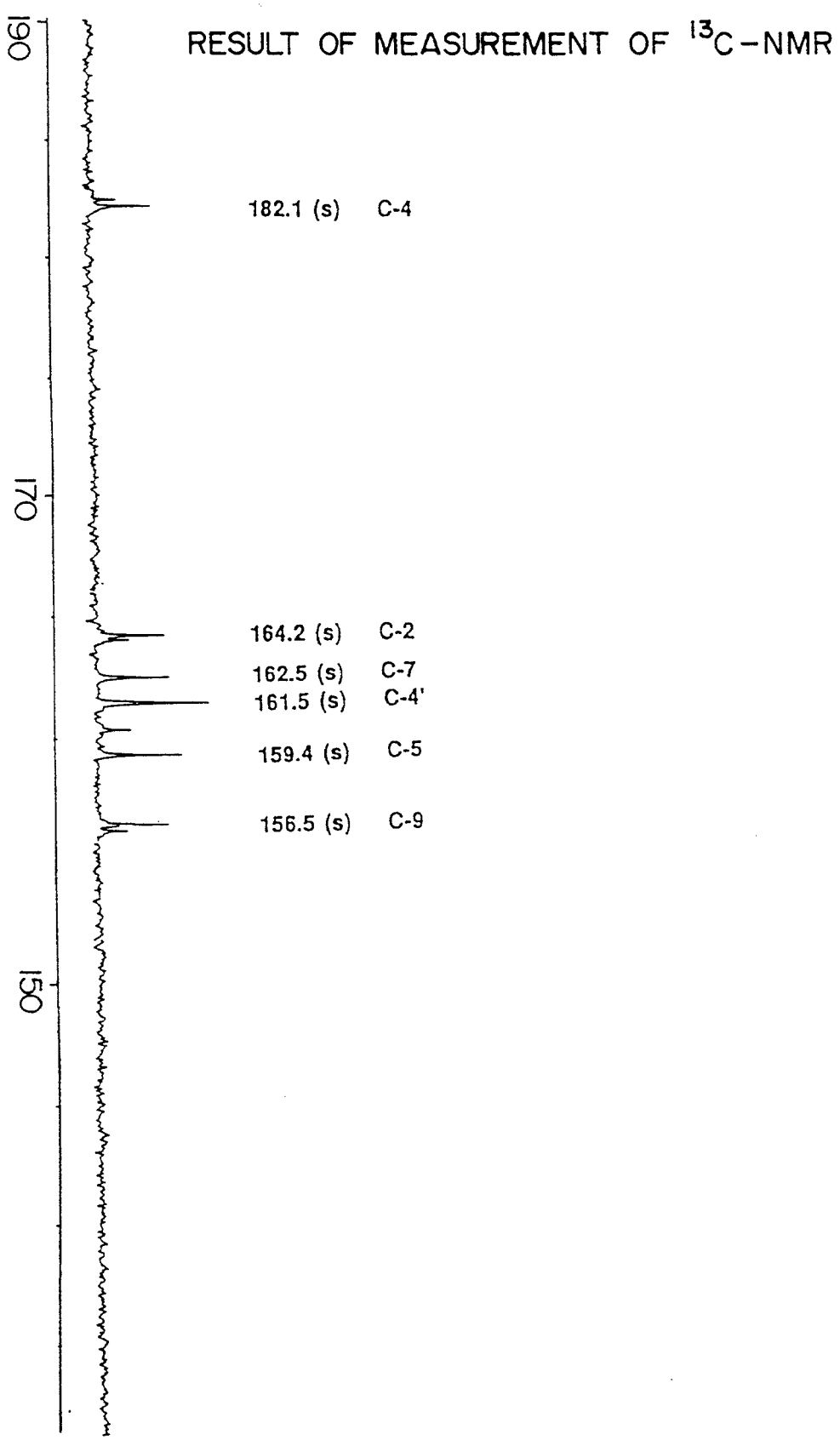

Further, $^{13}$C NMR spectrum (500 MHz) of the present substance was measured by GE OMEGA 300 type nuclear magnetic resonance spectrum absorption spectrometer using 25 mg of purified antioxidant substance and tetramethylsilane (TMS, (CH$_3$)$_4$Si) as an internal standard, and results shown in FIG. 5 were obtained. In FIG. 5, chemical shift was indicated by "δ". The purified antioxidant substance gave signal corresponding to 27 carbon atom in MeOH-d$_4$, which suggested the following structural formula:

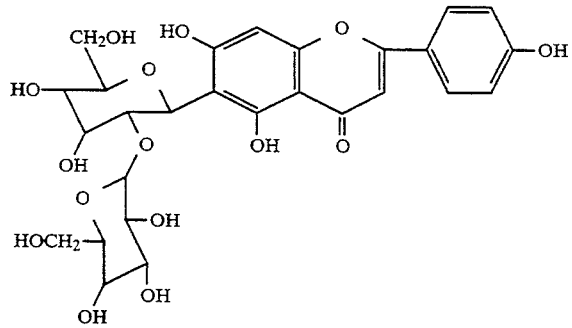

based on standard value of $^{13}$C-NMR for isovitexin (Remarathnam, N., Osawa, T., Namiki, M. and Kawakishi, S.: J. Agric. Food Chem., 37 316–319 (1989)).

From the above formula, the present substance is named 2'-O-glycosyl-isovitexin.

EXAMPLE 2

Fractionation and Preparation of Active Ingredient

Lyophilized powder (20 g) of green juice of wheat before ripening as treated in the same manner as in Example 1 to obtain 118 mg of 60% methanol-extract. Further, the extract was repeatedly recrystallized from 60% methanol to obtain 106 mg of pale yellow crystals. The present substance was found to be the same substance as that obtained in Example 1.

EXAMPLE 3

Fractionation and Preparation of Active Ingredient

Lyophilized powder (20 g) of green juice of comfrey before ripening was treated in the same manner as in Example 1 to obtain 40 mg of 60% methanol-extract. Further, the extract was repeatedly recrystallized from 60% methanol to obtain 37 mg of white crystals. The present substance was found to be the same substance as that obtained in Example 1.

EXAMPLE 4

Measurement of lipid peroxide by TBA method

To 7.5 mg of linoleic acid was added 0.22 mg of α-tocopherol or 0.22 mg of water-extract obtained in Example 1. Then 200 μl of Fenton's reagent ($FeCl_2$, $H_2O_2$) was added to each of the resulting mixture, and the mixtures thus obtained were incubated at 37° C. for 16 hours (total amount: 5 ml).

To 0.2 ml of each solution were added 0.2 ml of aqueous 8% SDS[1] solution, 1.5 ml of acetate buffer (pH 3.5) and 1.5 ml of an aqueous 0.67% TBA[2] solution, and the mixture was heated for 1 hour in a boiling water bath (95° to 100° C.).

Figure 6:
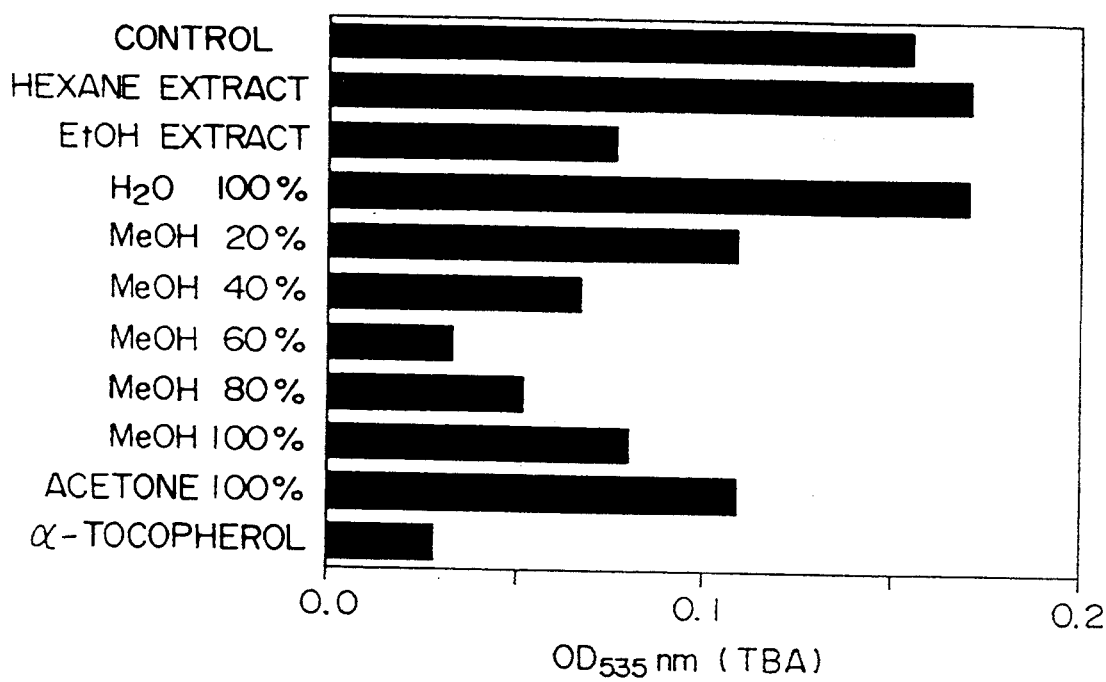
FIG. 6 is a graph illustrating results of measurements on lipid peroxides in each extract obtained in Example a and α-tocopherol by TBA method (results of measurement on optical density at 535 nm)

After cooling, 5 ml of butanol Was added. The resulting mixture was stirred vigorously and then the butanol layer was separated by centrifugation (2,000 rpm, 10 minutes), and optical density of the butanol layer was measured at 535 nm. Results obtained are shown in FIG. 6.

Notes:
1) SDS = sodium dodecylsulfate
2) TBA = thiobarbituric acid

EXAMPLE 5

Gas Chromatographic Analysis of Peroxide Product of Lipid, MAD[3] and 4NH4-Hydroxynonenal To microsomes and 7.5 mg of arachidonic acid was added 0.22 mg of α-tocopherol or 0.22 mg of antioxidant substance obtained in Example 1. To the mixture was added 5 ml of Tris hydrochloric acid buffer solution (05 M Trizma HCl, pH 7.4; 0.15 M KCl; 0.2% SDS). The resulting mixture was shaken mildly to make a suspension, to which was added 200μl of Fenton's reagent ($FeC_{12}$, $H_2O_2$). The mixture was reacted at 37° C. for 16 hours. After the reaction was stopped by addition of 50 1 of 4 % BHT[4]), 40μl of N-methylhydrazine and the reaction mixture was left to stand at room temperature for 1 hour to allow to produce an N-methylhydrazine derivative. After adding thereto 15 ml of saturated saline, the reaction mixture was extracted with 5 ml of dichloromethane for 3 hours.

The dichloromethane layer was separated, a predetermined amount of an internal standard solution for gas chromatography (I. S.) was added thereto, and dichloromethane was added to make exactly 10 ml to prepare a sample for gas chromatogrpahic analysis, which was subjected to gas chromatography under the following conditions:

| | |
|---|---|
| Capillary column: | DB-WAX |
| | 25 m × 0.25 mm |
| Column temperature: | 35° C. (retention time: 1.0 minutes) — 190° C. (retention time: 20 minutes) temperature elevation rate: 40° C./minute |
| Inlet temperature: | 250° C. |
| Detector temperature: | 300° C. |
| Detector: | NPD (nitrogen-phosphorus detector) |
| Carrier Gas: | Helium |

Figure 7:
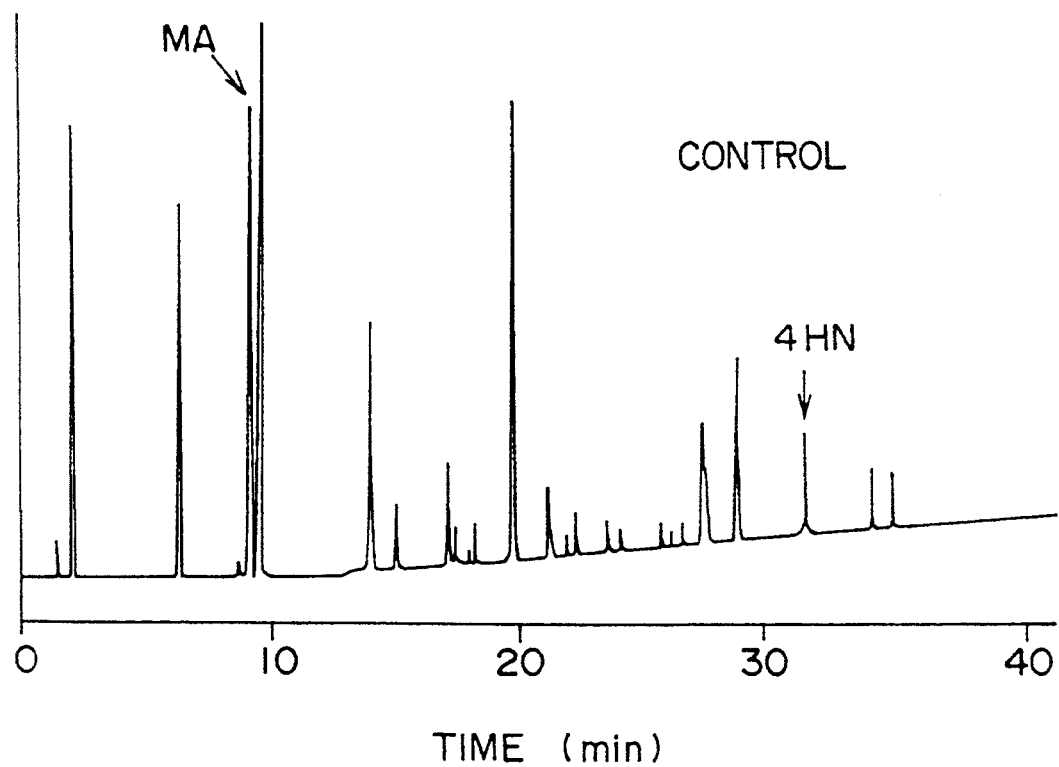
FIG. 7 is a gas chromatograph chart for lipid peroxides derived from arachidonic acid with Fenton's reagent, MA and 4HN.
Figure 8:
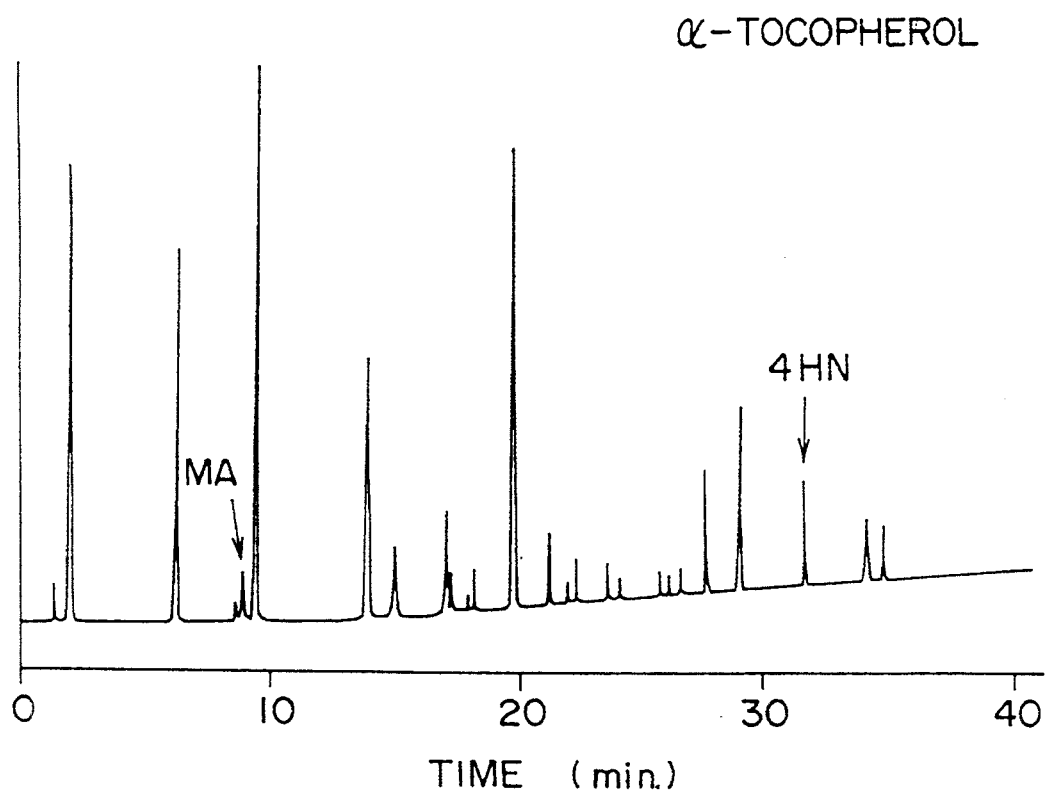
FIG. 8 is a gas chromatograph chart for lipid peroxides derived from arachidonic acid with Fenton's reagent, MA and 4HN.
Figure 9:
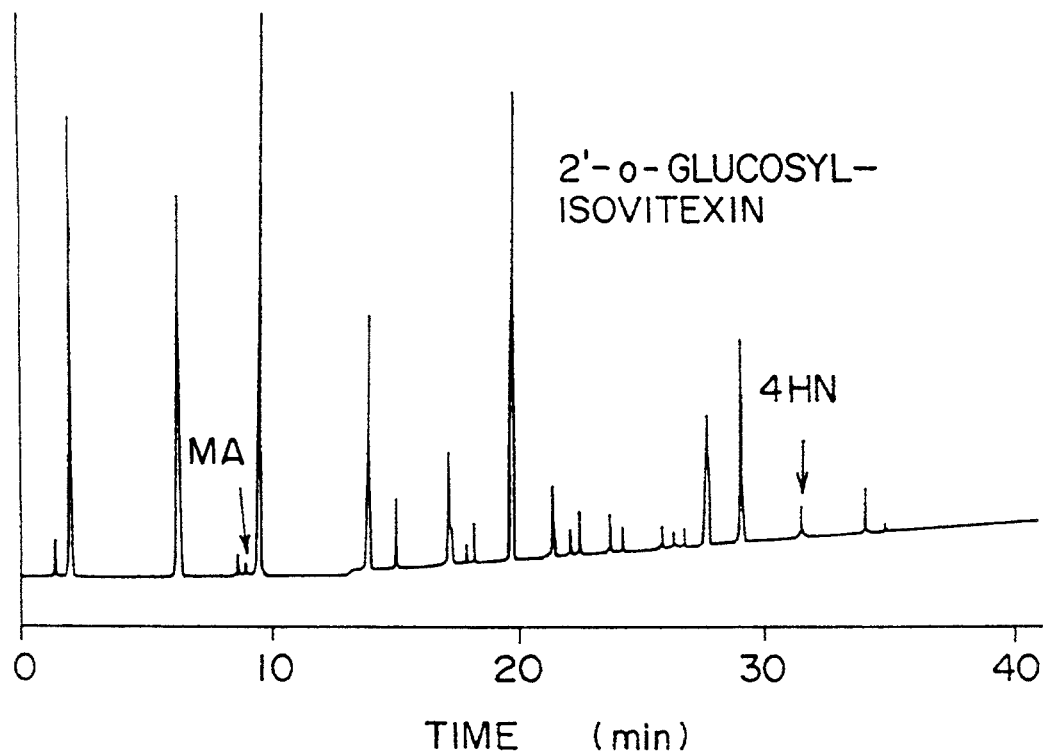
FIG. 9 is a gas chromatograph chart for lipid peroxides derived from arachidonic acid with Fenton's reagent, MA and 4HN.

The results obtained are shown in FIGS. 7 to 9. From the chromatographic charts, it revealed that the antioxidant substance of the present invention having a structure corresponding to isovitexin to which one molecule of glucose is connected strongly inhibits the production of not only MAD but also 4HN (4-hydroxynonenal) and has an antioxidant activity more potent than α-tocopherol.

Notes:
3) MAD = malondialdehyde
4) BHT = butylhydroxytoluene

EXAMPLE 6

To the powder (100 g) of green juice obtained in Example 1 was added 2.5 liters of n-hexane, and the mixture was stirred at room temperature for about 5 minutes. Insoluble matter as separated by centrifugation (8,000 rpm, 10 minutes) and 2.5 liters of n-hexane was added thereto. This procedure was repeated to obtain n-hexane insoluble component.

To the insoluble component was added 2.5 liters of aqueous ethanol solution having a water content of 20 v/v %, and extraction was repeated similarly to the above-described procedure to obtain 20 v/v % (water content) ethanol-soluble component. After distilling off ethanol under reduced pressure, 72 g of a fraction which was able to be extracted with aqueous ethanol solution having a water content of 20 v/v % ethanol.

This fraction (60 g) was adsorbed by Amberlite XAD-2 column and then serially eluted with distilled water, aqueous methanol solution having water contents of 80 v/v %, 60 v/v %, 40 v/v % 20 v/v % and 0 v/v %, respectively, and acetone.

The solvents were distilled off from the elutes under reduced pressure to obtain 27 g of water-extract, 1.1 g of 20% methanol-extract, 680 mg of 40% methanol-extract, 1.5 g of 60% methanol-extract, 170 mg of 80% methanol-extract which was prepared similarly was recrystallized to obtain 1.2 g of 2'-O-glucosyl-isovitexin.

Model juices containing β-carotene having compositions as shown in Tables 1 and 2 were prepared, and antioxidant activities of 60% methanol-extract and 2'-O-glucosyl-isovitexin, respectively, at pH 3 or 5 on β-carotene were measured using water and vitamin C as control.

Determination of β-carotene was performed based on the method prescribed in Hygienic Examination Methods, Commentary, ed. Japan Pharmaceutical Association, p.347–349 (1990) published by Kinbara Shuppan Co., Ltd.).

TABLE 1

| Composition of Model Juice | |
|---|---|
| Component | Composition |
| Inverted sugar | 20.0 g |
| Citric acid, anhydrous | 1.0 g |
| β-Carotene* | 0.65 g |
| H₂O to make | 100 ml |
| pH adjusted to | 3.0 |

Note:
*carotene base: produced by Sanei Kagaku Kogyo Co., Ltd.

TABLE 2

| Composition of Model Juice | |
|---|---|
| Component | Composition |
| Inverted sugar | 20.0 g |
| Citric acid (dihydrate) | 0.43 g |
| Sodium citrate (dihydrate) | 1.23 g |
| β-Carotene* | 0.656 mg |
| H₂O to make | 100 ml |
| pH adjusted to | 5.05 |

Note:
*carotene base: produced by Sanei Kagaku Kogyo Co., Ltd.

Tables 3 and 4 show antioxidant activities of the respective fractions on β-carotene. The reaction temperature was 18° C.

TABLE 3

| | Antioxidant Activity at pH 3 | |
|---|---|---|
| | Residual Ratio (%) of β-Carotene | |
| Antioxidant | Day 0 | Day 7 |
| Water | 100 | 18.0 |
| L-Ascorbic acid: 0.17 mM | 100 | 44.8 |
| 2'-O-Glucosyl-isovitexin: 0.17 mM* | 100 | 55.0 |
| 60% Methanol-fraction: 0.17 mM* | 100 | 52.0 |

Note:
*Expressed as amount of 2'-O-glucosyl-isovitexin.

TABLE 4

| | Antioxidant Activity at pH 5 | |
|---|---|---|
| | Residual Ratio (%) of β-Carotene | |
| Antioxidant | Day 0 | Day 7 |
| Water | 100 | 0 |
| L-Ascorbic acid: 0.17 mM | 100 | 30.0 |
| 2'-O-Glucosyl isovitexin: 0.17 mM* | 100 | 41.0 |
| 60% Methanol-fraction: 0.17 mM* | 100 | 44.5 |

Note:
*Expressed as amount of 2'-O-glucosyl isovitexin.

Further, juice containing 2'-O-glucosyl-isovitexin and 60% methanol-extract fraction showed no color change both at pH 3 and at pH 5 and retained always fresh pale red color while juice containing no anti-oxidant showed considerable color fading at pH 3 and became colorless at pH 5.

EXAMPLE 7

After being washed, green leaves of barley were sucked to obtain green juice, which was then powderized by a suitable drying method such as spray-drying, lyophilization or the like. The green juice powder thus obtained (10 kg) was extracted twice each with 200 liters of hexane. Water (100 liters) was added to hexane-insoluble portion and water-soluble component was spray-dried to obtain 3.8 kg of spray-dried product. Then, 100 liters of aqueous ethanol solution having a water content of 20 v/v % was added thereto obtain 2.7 kg of 20% (water content) ethanol-soluble component, from which ethanol was distilled off. To this were added 70 liters of an aqueous methanol solution having a water content of 40 v/v % to extract 40% (water content) methanol-soluble component, and then methanol was distilled off to obtain 2 kg of 40% (water content) methanol-soluble component. This component was named substance A. To 100 g of substance A was added 400 g of talc to prepare a suspension, which was then spray-dried at an air absorption temperature of 180° C. and an air exhaustion temperature of 120° C. to produce 470 g of powdery raw material.

EXAMPLE 8

A solution containing 100 g of substance A obtained in Example 7 and 400 g of dextrin was prepared, which was spray-dried at an air absorption temperature of 190° C. and an air exhaustion temperature of 120° C. to obtain 430 g of powdery raw material.

EXAMPLE 9

Water (300 ml) was added to 100 g of Lintex-P (Sanraku Co., Ltd.) and the mixture was kneaded to form a slurry. Methanol fractionation as in Example 6 was exactly performed stepwise to separate a substance which as a fraction extracted with an aqueous methanol having a water content of 40%. This substance was recrystallized from an aqueous methanol having a water content of 40% to obtain 2'-O-glucosyl-isovitexin. The 2'-O-glucosyl-isovitexin (40 g) thus obtained was added to the slurry and stirred at room temperature for 90 minutes, followed by spray-drying at an air absorption temperature of 170° C. and an air exhaustion temperature of 110° C. to obtain 127 g of powdery raw material as a cyclodextrin inclusion compound.

EXAMPLE 10

Kaolin (200 g) was mixed with 100 g of sub-stance A obtained in Example 7 to prepare a 30% suspension, which was then spray-dried at an air absorption temperature of 170° C. and an air exhaustion temperature of 110° C. to obtain 270 g of powdery raw material.

EXAMPLE 11

After being desalted, 100 ml of a 4% sodium silicate solution was adjusted to pH 9 with 1% potassium hydroxide, and 15 ml aliquot thereof was heated at 95° C. for 15 minutes. Then, 10 g of 2'-O-glucosyl-isovitexin obtained by the method of Example 1 was portionwise added to 85 ml of the sodium silicate solution which remained, and then concentrated at 90° C. for 8 hours to produce spherical silica containing the antioxidant substance.

EXAMPLE 12

After being washed with water, sterilized and washed again with water, 100 kg of young leaves of barley were crushed with a crusher and sucked with a sucker to obtain about 95 liters of young barley leaf extract. This young barley leaf extract was spray-dried to obtain 4 kg of green juice powder, which was then extracted with 20 liters of an aqueous ethanol solution having a water content of 20%, followed by removal of the solvent to obtain 700 g of a liquid extract.

As a result of analysis, the extract was found to contain 2'-O-glucosyl-isovitexin in a concentration of 0.7% by weight. This extract was diluted with water to prepare an aqueous solution having a concentration of 100 mg/liter expressed in terms of 2'-O-glucosyl-isovitexin.

In this aqueous solution was immersed a Kabosu fruit (a kind of citrus fruit, Citrus sphaerocarpa hort. ex Tanaka) for 30 minutes and then taken out and left to stand at room temperature. Therefore, freshness retention tests were performed using water, vitamin C and vitamin E as controls by visual evaluation of the color of the kabosu fruit after lapse of a predetermined time, judging green as A, partially yellowing as B, and wholly yellowing as C. The results obtained are shown in Table 5.

TABLE 5

Freshness Retention Test on Kabosu Fruit

| | Day Number | | | |
|---|---|---|---|---|
| | Day 0 | Day 7 | Day 14 | Day 20 |
| Water | A | B | C | C |
| Vitamin C* | A | A | B | B-C |
| Vitamin E** | A | A | B | B-C |
| Extract | A | A | A | A |

Notes:
*500 mg/liter
**E mix P-20, 500 mg/liter as vitamin E

EXAMPLE 13

The extract (100 g obtained in Example 12 was extracted with an aqueous methanol solution having a water content of 40 and dried to obtain 65 g of an extract. Using this extract, freshness retention tests were performed on sudachi fruit (a kind of a citrus fruit, Citrus sudachi hort. ex Shirai) similarly to Example 12. The results obtained are shown in Table 6.

TABLE 6

Freshness Retention Test on Sudachi Fruit

| | Day Number | | | |
|---|---|---|---|---|
| | Day 0 | Day 7 | Day 14 | Day 20 |
| Water | A | B | C | C |
| Vitamin C* | A | B | B | C |
| Vitamin E** | A | B | B | C |
| Extract | A | A | A | B |

Notes:
*500 mg/liter
**E mix P-120, 500 mg/liter as vitamin E.

EXAMPLE 14

A component soluble in an aqueous ethanol solution having a water content of 20% prepared in the same manner as in Example 7 was formulated as set forth below to obtain a beverage. After preparation, the resulting juice was sterilized with heating at 85° C. for 30 minutes.

| | |
|---|---|
| Granulated sugar | 20 g |
| Fructose | 35 g |
| Citric acid | 3 g |
| Succinic acid | 0.1 g |
| Component soluble in an aqueous ethanol solution having a water content of 20% | 10 g |
| Perfume | suitable amount |
| To make | 1 liter |

This preparation was a beverage which had a favorable fragrance and was effective for the suppression of foul breath.

EXAMPLE 15

The component soluble in an aqueous ethanol solution having a water content of 20% prepared in Example 7 was adsorbed on Amberlite XAD-2 column and eluted with an aqueous methanol solution having a water content of 40%. The fraction obtained was dried and blended with a juice having the following composition to obtain a beverage. After preparation, the resulting juice was sterilized with heating at 85° C. for 30 minutes.

| | |
|---|---|
| Granulated sugar | 20 g |
| Fructose | 35 g |
| Citric acid | 3 g |
| Tartaric acid | 0.1 g |
| β-Carotene (carotene base No. 31256 produced by Sanei Kagaku Kogyo Co., Ltd.) | 10 mg |
| Fraction eluted with an aqueous methanol solution having a water content of 40% | 0.5 g |
| Perfume | suitable amount |
| To make | 1 liter |

After leaving this formation to stand under natural light for 15 days, β-carotene remained in an amount of 83%. On the other hand, β-carotene disappeared completely in a formulation in which the fraction eluted with an aqueous methanol solution having a water-content of 40% was absent. Determination of β-carotene was performed based on the method prescribed in Hygienic Examination Methods, Commentary, ed. Japan Pharmaceutical Association, p.347–349 (1990) published by Kinbara Shuppan Co., Ltd.).

EXAMPLE 16

A juice was prepared by repeating the procedure of Example 15 except that 0.01% 2'-O-glucosyl-isovitexin was added instead of the aqueous methanol solution having a water content of 40%. After leaving this formulation to stand under natural light for 15 days, β-carotene remained in an amount of 73.2% while in a juice in which 2'-O-glucosyl-isovitexin was absent β-carotene disappeared completely.

EXAMPLE 17

Corned beef was prepared by providing beef meat, removing fat therefrom, adding salt thereto, preserving for 5 days, cooking to loosen meat fibers, and adding the fraction eluted with an aqueous methanol solution having a water content of 40% in an amount of 0.1% together with table salt, spices, fats, seasonings. The corned beef thus prepared was stored in a refrigerator for 10 days. As a result, the preparation in which the fraction eluted with an aqueous methanol solution having a water content of 40% was absent changed color considerably due to oxidation while the preparation of the invention retained fresh pink color immediately after production.

EXAMPLE 18

Upon preparation of margarine by a conventional method, the extract with an aqueous ethanol solution having a water content of 20% was added in a proportion of 10 g/1,000 g of margarine, and the margarine obtained was preserved at room temperature for 3 months. The preparation containing no such fraction suffered denaturation and its fragrance changed resulting in that it was unsuitable for use for food while the margarine of the present invention containing the fraction suffered substantially no such change in fragrance.

EXAMPLE 19

During preparing solid yoghurt by a conventional method, 0.2% of the fraction extracted with an aqueous ethanol solution having a water content of 20% was added. The yoghurt was filled in a small vessel and incubated therein to prepare a yoghurt preparation. This preparation had a unique favorable fragrance and was stable after preservation for a long time.

EXAMPLE 20

A liquid yoghurt was prepared by preparing and incubating a yoghurt by a conventional method, and then adding 0.01% of β-carotene and 0.02% of 2'-O-glucosylisovitexin. After superimposing the preparations thus obtained one on another and exposing them to the direct rays of the sun for 3 days, no decoloration occurred.

EXAMPLE 21

To durum wheat flour (7 kg) was mixed with 3 kg of a high protein content wheat flour, and the mixture was charged in a mixer, and 0.025 g of the extract with an aqueous ethanol solution having a water content of 20% obtained in Example 7 was added. After adding thereto 2.5 kg of water at about 40° C., the mixture was kneaded and extruded through an extruder while being stirred, and dried and cut to a constant length to produce spaghetti containing an antioxidant substance.

EXAMPLE 22

To a mixture of high protein content wheat flour (350 g), 20 g of granulated sugar, 3.4 g of yeast, 5 g of water, and 25 g of butter was added 0.7 g of the extract with an aqueous ethanol solution having a water content of 20% obtained in Example 7, and the resulting formulation was treated under conventional conditions for baking bread to obtain bread containing an antioxidant substance.

EXAMPLE 23

After being washed, young green leaves of barley were sucked to obtain green juice, which was then powderized by spray-drying to obtain 1 kg of green juice powder. This was extracted twice each with 20liters of hexane. Water (10 liters) was added to hexane insoluble portion and water-soluble component was spray-dried to obtain 380 g of spray-dried product. Then, 10 liters of an aqueous ethanol solution having a water content of 20% was added thereto to obtain 300 g of component soluble in an aqueous ethanol solution having a water content of 20%, from which ethanol was distilled off. To this were added 10 liters of an aqueous methanol solution having a water content of 40% to extract a component soluble in an aqueous methanol solution having a water content of 40%, and then methanol was distilled off to obtain 250 g of a component soluble in an aqueous methanol solution having a water content of 40%. This component was named substance A. Using substance A which was soluble in water and in aqueous alcohol solutions, a lotion having the following composition was prepared:

| | |
|---|---|
| Substance A | 5 g |
| 95% Ethanol | 100 g |
| Methyl p-hydroxybenzoate | 0.05 g |
| Perfume | 0.5 g |
| Colorant | 0.005 g |
| Purified water | suitable amount |
| Total to make | 1,000 g |

APPLICATION EXAMPLE 1

The lotion prepared in Example 23 was used everyday after washing face in the morning and before sleeping to examine effects on improvement of spots and freckles. Results obtained on a panel of 30 women are shown in Table 7. The tests were performed in a period of 6 months. Evaluation was made on the following criteria. Color of spots and freckles:

| | |
|---|---|
| Brown: | No effect |
| Pale brown: | Slightly effective |
| Almost gone: | Effective |

Boundary between spot or freckle portion and other portion:

| | |
|---|---|
| Boundary apparent: | No effect |
| Boundary unclear: | Slightly effective |
| Boundary almost: undiscernible | Effective |

TABLE 7

| | Slightly effective | Effective | No effect |
|---|---|---|---|
| Color | 15 | 7 | 8 |
| Boundary | 17 | 8 | 5 |

EXAMPLE 24

The methanol fractionation as in Example 23 was exactly performed stepwise to separate substance A which was a fraction eluted with an aqueous methanol solution having a water content of 40%. The present substance was recrystallized from an aqueous methanol solution having a water content of 40% to obtain 2'-O-glucosylisovitexin, which was added to the formulation for lotion described in Example 23 instead of substance A in a concentration of 0.1% to prepare a lotion.

EXAMPLE 25

| Formulation of Cream: | |
|---|---|
| Stearic acid | 10 g |
| Isopropyl myristate | 5 g |
| Cetyl alcohol | 5 g |
| Liquid paraffin | 7 g |
| Glycerol monostearate | 2 g |
| Polyoxyethylene stearate | 5 g |
| Methyl p-hydroxybenzoate | 0.1 g | were mixed and to the mixture were added 3 g of glycerol, 1 g of propylene glycol, and 50 g of water. The resulting mixture was emulsified and when the temperature of the emulsion reached 60° C., 0.3 g of 2'-O-glucosyl-isovitexin obtained in Example 1 was added, following by addition of a small amount of perfume while stirring to prepare a cream.

APPLICATION EXAMPLE 2

The cream prepared in Example 25 was used for 6 months everyday after washing face in the morning and before sleeping to examine effects on improvement of spots and freckles as well as chapping. Results obtained on a panel of 30 men an 30 women are shown in Table 7. Judgement on spots and freckles was made in the same manner as in Application Example 1 of Example 23 while chapping was judged based on slipping of cream on skin by touching on the following criteria.

| | |
|---|---|
| No effect: | Rough touch on the skin surface |
| Slightly: effective | Rough touch remains slightly, but the cream spreads well. |
| Effective: | The cream spreads well on the skin surface. |

The results obtained are shown in Tables 8 and 9.

TABLE 8

| Men | | | | | | |
|---|---|---|---|---|---|---|
| | Number of Months for which Cream Was Applied | | | | | |
| | 1 M | 2 M | 3 M | 4 M | 5 M | 6 M |
| No effect | 20 | 20 | 17 | 11 | 11 | 10 |
| Slightly effective | 10 | 8 | 9 | 15 | 12 | 11 |
| Effective | — | 2 | 4 | 4 | 7 | 9 |

TABLE 9

| Women | | | | | | |
|---|---|---|---|---|---|---|
| | Number of Months for which Cream Was Applied | | | | | |
| | 1 M | 2 M | 3 M | 4 M | 5 M | 6 M |
| No effect | 23 | 20 | 18 | 10 | 7 | 5 |
| Slightly effective | 7 | 10 | 10 | 14 | 15 | 15 |
| Effective | — | — | 2 | 6 | 8 | 10 |

EXAMPLE 26

Using 2'-O-glucosyl-isovitexin obtained by the method of Example 1, a hair growing agent of the following formation was prepared:

2'-O-Glucosyl-isovitexin (0.1 g) was dissolved in 95 ml of an aqueous 66% ethanol solution, and 5 ml of propylene glycol, 0.1 g of perfume, and 0.1 g of colorant were added to the resulting solution to prepare a hair growing agent.

APPLICATION EXAMPLE 3

Effects of the hair growing agent obtained in Example 26 were examined on a panel of 20 men and 20 women. Effects after 6 month every day application of the hair growing agent were judged according to the following criteria:

| Dandruff | | Thin Hair State | |
|---|---|---|---|
| Class (State) | Rating | Class (State) | Rating |
| Very much | −3 | Very much | −3 |
| Much | −2 | Much | −2 |
| Medium | −1 | Medium | −1 |
| Normal | 0 | Normal | 0 |
| Slight | +3 | Slight | +3 |

| Color, Gloss | |
|---|---|
| Class (State) | Rating |
| Bad | −3 |
| Normal | 0 |
| Good | +3 |

Based on the aforementioned criteria the states before and after the application are shown in Table 10.

TABLE 10

| | | Before Application | | | After Application | | |
|---|---|---|---|---|---|---|---|
| Sex | Age | Dandruff | Thin Hair | Color, Gloss | Dandruff | Thin Hair | Color, Gloss |
| ♂ | 30 | −1.5 | −1 | −3 | 0 | −1 | 0 |
| ♂ | 27 | −2 | −1 | 0 | −1 | 0 | +3 |
| ♂ | 23 | −2 | −1 | 0 | −1 | 0 | +3 |
| ♂ | 35 | −1.5 | −1 | 0 | 0 | 0 | +1.5 |
| ♂ | 40 | −1 | −2 | 0 | 0 | −1 | +1.5 |
| ♂ | 53 | −1 | −2 | −3 | 0 | −1.5 | 0 |
| ♂ | 43 | 0 | −3 | −3 | 0 | −2.5 | 0 |
| ♂ | 43 | −1 | −2 | 0 | 0 | −1.5 | 0 |
| ♂ | 48 | −2 | −2 | −3 | −1 | −1 | +1.5 |
| ♂ | 55 | −1 | −3 | −3 | 0 | −2.5 | +1.5 |
| ♂ | 52 | −1 | −3 | −3 | +3 | −2 | +1.5 |
| ♂ | 38 | −1 | −2 | −3 | 0 | −1 | 0 |
| ♂ | 35 | −1.5 | −1 | 0 | −1 | −1 | 0 |
| ♂ | 37 | −1.5 | −2 | 0 | 0 | −1 | 0 |
| ♂ | 40 | −1 | −3 | −3 | 0 | −2 | +1.5 |
| ♂ | 45 | −1 | −2 | −3 | 0 | −1.5 | +1.5 |
| ♂ | 43 | −1 | −2 | −3 | 0 | −1 | +1.5 |
| ♂ | 56 | −1 | −2 | −3 | 0 | −1 | +1.5 |
| ♂ | 54 | −2 | −1 | 0 | −1 | −1 | +1.5 |
| ♂ | 55 | −2 | −2 | −3 | −1 | −1.5 | 0 |
| ♂ | 55 | −2 | −2 | −3 | −1 | −1.5 | 0 |
| ♀ | 30 | −2 | 0 | +3 | 0 | 0 | +3 |
| ♀ | 35 | −2 | 0 | 0 | −1 | 0 | +2 |
| ♀ | 37 | −3 | 0 | 0 | −1 | 0 | +3 |
| ♀ | 40 | −1 | 0 | −3 | 0 | 0 | 0 |
| ♀ | 40 | −2 | 0 | −1.5 | 0 | 0 | 0 |
| ♀ | 43 | −2 | 0 | −1.5 | −1 | 0 | 0 |
| ♀ | 45 | −1 | 0 | −1.5 | 0 | 0 | +3 |
| ♀ | 47 | −2 | −1 | −1 | −2 | +1.5 | +3 |
| ♀ | 47 | −2 | 0 | −2 | 0 | 0 | +1 |
| ♀ | 47 | −2 | −1 | −2 | 0 | 0 | 0 |
| ♀ | 50 | −3 | 0 | −3 | 0 | 0 | 0 |
| ♀ | 50 | −2 | −1 | −2 | 0 | 0 | 0 |
| ♀ | 50 | −1 | −1 | −3 | 0 | −1 | +1.5 |
| ♀ | 51 | −3 | −1 | −1.5 | −1.5 | 0 | 0 |
| ♀ | 52 | −2 | −1 | −2 | 0 | 0 | 0 |
| ♀ | 52 | −3 | −1 | −3 | 0 | 0 | +1.5 |
| ♀ | 53 | −2 | −2 | −3 | −1 | −1 | 0 |
| ♀ | 54 | −1 | −1 | −3 | 0 | 0 | +1.5 |
| ♀ | 55 | −1 | −1 | −3 | 0 | 0 | +1.5 |
| ♀ | 56 | −2 | −2 | −3 | 0 | 0 | 0 |

What is claimed is:

1. A method of extracting 2'-O-glucosyl-isovitexin of formula:

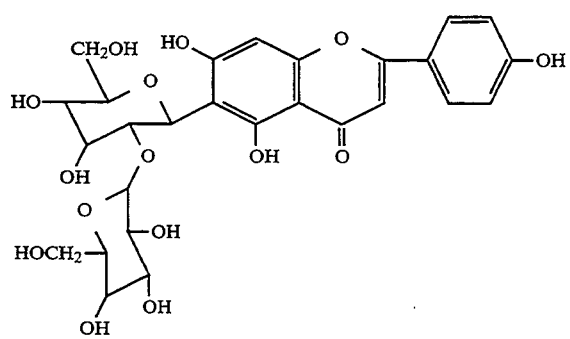

from green leaves of a green leaf plant, which comprises the steps of
- crushing the green leaves of a plant of the Gramineae family to obtain a green juice from the green leaves, drying the green juice to obtain a dry powder, contacting the dry powder with n-hexane to recover a fraction (a) which is insoluble in the n-hexane,
- extracting the fraction (a) with an aqueous ethanol solution with a water content of 0–80% to recover a fraction (b) which is soluble in the aqueous ethanol solution,
- adsorbing the fraction (b) on a resin adsorbent and then eluting it with an aqueous methanol solution with a water content of 0–80% to recover a fraction (c) which is soluble in the aqueous methanol solution, and
- treating the fraction (c) with an aqueous methanol solution with a water content of 30–70% and crystallizing 2'-O-glucosyl-isovitexin.

2. A method of extracting 2'-O-glucosyl-isovitexin of the formula:

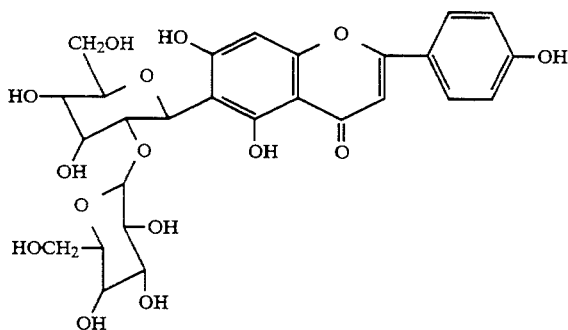

from green leaves of a green leaf plant which comprises the steps of:
- crushing the green leaves of a plant of the Gramineae family to obtain a green juice from the green leaves and drying the green juice to obtain a dry powder,
- contacting the dry powder with n-hexane and recovering an n-hexane insoluble component,
- contacting the n-hexane insoluble component with an aqueous ethanol solution and recovering an aqueous ethanol fraction containing an aqueous ethanol soluble component,
- separating the ethanol from the aqueous ethanol fraction and recovering the aqueous ethanol soluble component,
- contacting the separated aqueous ethanol soluble component with an aqueous methanol solution and recovering an aqueous methanol soluble fraction containing an aqueous methanol soluble component, and
- separating methanol from the aqueous methanol fraction and recovering 2'-O-glucosyl-isovitexin having the above formula.

3. The method of claim 2 wherein the green leaf plant is a member selected from the group consisting of barley, wheat, rye, oats, gromwell-reed, corn, millet and Italian dry-grass.

4. The method of claim 2 wherein the green leaf plant is a member selected from the group consisting of barley and wheat.

5. The method of claim 2 wherein the aqueous ethanol solution contains 10–70% by volume of water.

6. The method of claim 2 wherein the ethanol is separated from the ethanol soluble component by adsorption of the ethanol soluble component on a resin adsorbent.

7. The method of claim 2 wherein the ethanol is separate from the ethanol soluble component by evaporating or distilling the ethanol from the ethanol fraction.

8. The method of claim 2 wherein the aqueous methanol solution contains 20 to 70% by volume of water.

9. A method of extracting 2'-O-glucosyl-isovitexin of the formula:

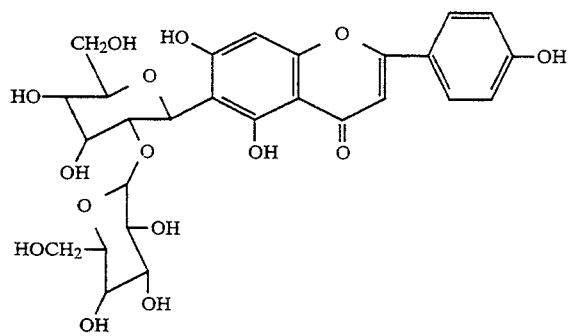

from green leaves of a green leaf plant which comprises the steps of:
- crushing the green leaves of a plant of the Gramineae family to obtain a green juice form the green leaves, and drying the green juice to obtain a dry powder,
- contacting the dry powder with an aqueous ethanol solution and recovering an aqueous ethanol fraction containing an aqueous ethanol soluble component,
- separating the ethanol from the aqueous ethanol fraction and recovering an aqueous ethanol soluble component,
- contacting the separated aqueous ethanol soluble component with an aqueous methanol solution and recovering an aqueous methanol soluble fraction containing an aqueous methanol soluble component and,
- separating methanol from the aqueous methanol fraction and recovering 2'-O-glucosyl-isovitexin having the above formula.

10. The method of claim 9 wherein the green leaf plant is a member selected from the group consisting of barley, wheat, rye, oats, gromwell-reed, corn, millet and Italian dry-grass.

11. The method of claim 9 wherein the green leaf plant is a member selected from the group consisting of barley and wheat.

12. The method of claim 9 wherein the aqueous ethanol solution contains 10–70% by volume of water.

13. The method of claim 9 wherein the ethanol is separated from the ethanol soluble component by adsorption of the ethanol soluble component on a resin adsorbent.

14. The method of claim 9 wherein the ethanol is separate from the ethanol soluble component by evaporating or distilling the ethanol from the ethanol fraction.

15. The method of claim 9 wherein the aqueous methanol solution contains 20 to 70% by volume of water.

* * * * *